US009125977B2

(12) United States Patent
Nishimura et al.

(10) Patent No.: US 9,125,977 B2
(45) Date of Patent: Sep. 8, 2015

(54) ARTIFICIAL HEART CONTROL DEVICE, ARTIFICIAL HEART SYSTEM AND ARTIFICIAL HEART CONTROL METHOD

(75) Inventors: Takashi Nishimura, Tokyo (JP); Daisuke Ogawa, Nagano (JP); Tomoya Kitano, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 650 days.

(21) Appl. No.: 12/997,288

(22) PCT Filed: Apr. 15, 2009

(86) PCT No.: PCT/JP2009/057552
§ 371 (c)(1),
(2), (4) Date: Jan. 29, 2011

(87) PCT Pub. No.: WO2009/150893
PCT Pub. Date: Dec. 17, 2009

(65) Prior Publication Data
US 2011/0112354 A1    May 12, 2011

(30) Foreign Application Priority Data
Jun. 11, 2008   (JP) .................................. 2008-153556

(51) Int. Cl.
*A61N 1/362*     (2006.01)
*A61M 1/10*      (2006.01)
(Continued)

(52) U.S. Cl.
CPC .............. *A61M 1/1086* (2013.01); *A61M 1/008* (2013.01); *A61M 1/1005* (2013.01); *A61M 1/122* (2013.01); *A61M 1/101* (2013.01); *A61M 1/12* (2013.01); *A61M 2230/04* (2013.01); *A61N 1/362* (2013.01)

(58) Field of Classification Search
CPC ....... A61N 1/362; A61N 1/365; A61N 1/372; A61N 1/375; A61M 1/00; A61M 1/10; A61M 1/12
USPC ................. 600/16–18; 415/900; 623/3.1–3.3; 604/6.11
See application file for complete search history.

(56) References Cited

U.S. PATENT DOCUMENTS

| 4,957,504 A | 9/1990 | Chardack |
| 6,443,884 B1 | 9/2002 | Miyawaki |

(Continued)

FOREIGN PATENT DOCUMENTS

| JP | 3212269 A | 9/1991 |
| JP | 7265412 A | 10/1995 |

(Continued)

OTHER PUBLICATIONS

International Search Report for PCT/JP2009/057552 mailed Jul. 7, 2009.

(Continued)

*Primary Examiner* — Christopher D Koharski
*Assistant Examiner* — Elizabeth K So
(74) *Attorney, Agent, or Firm* — Lowe Hauptman & Ham, LLP

(57) ABSTRACT

Provided is an artificial heart control device for controlling a blood pump which assists flow of blood in a heart, the artificial heart control device including: a timing detection part which is configured to detect reference timing within a cardiac cycle of the heart; and a blood pump control part which is configured to control a rotational speed of the blood pump, wherein the blood pump control part controls, with reference to the reference timing detected by the timing detection part, the rotational speed of the blood pump such that the rotational speed becomes a rotational speed corresponding to a predetermined control pattern. According to the present invention, it is possible to provide an artificial heart control device, an artificial heart system and an artificial heart control method which can provide a load control optimum for the recovery of functions of a patient's own heart.

18 Claims, 12 Drawing Sheets

(51) Int. Cl.
*A61M 1/00* (2006.01)
*A61M 1/12* (2006.01)

(56) References Cited

U.S. PATENT DOCUMENTS

| | | |
|---|---|---|
| 7,150,711 B2 | 12/2006 | Nuesser et al. |
| 2003/0045772 A1 | 3/2003 | Reich et al. |
| 2005/0019167 A1 | 1/2005 | Nusser et al. |
| 2005/0071001 A1 | 3/2005 | Jarvik |
| 2007/0142923 A1 | 6/2007 | Ayre et al. |
| 2007/0265703 A1* | 11/2007 | Sutton et al. ............ 623/3.1 |
| 2008/0015403 A1 | 1/2008 | Trumble |
| 2010/0268333 A1* | 10/2010 | Gohean et al. ............ 623/3.14 |

FOREIGN PATENT DOCUMENTS

| | | |
|---|---|---|
| JP | 2000126282 A | 5/2000 |
| JP | 2002224066 A | 8/2002 |
| JP | 2005058617 A | 3/2005 |
| JP | 2005066013 A | 3/2005 |
| JP | 2005514962 T | 5/2005 |
| JP | 2008018242 A | 1/2008 |
| WO | 9951285 A1 | 10/1999 |

OTHER PUBLICATIONS

Supplementary European Search Report dated Oct. 31, 2014, corresponding to European patent application No. 09762324.

* cited by examiner

ARTIFICIAL HEART CONTROL DEVICE, ARTIFICIAL HEART SYSTEM AND ARTIFICIAL HEART CONTROL METHOD

RELATED APPLICATIONS

The present application is national phase of International Application Number PCT/JP2009/057552 filed Apr. 15, 2009, and claims priority from, Japanese Application Number 2008-15355 filed Jun. 11, 2008.

TECHNICAL FIELD

The present invention relates to an artificial heart control device, an artificial heart system and an artificial heart control method.

BACKGROUND OF THE INVENTION

Along with the progress of medical technology in recent years, the number of cases has increased where cardiopathy which has been considered as a serious disease can be cured. On the other hand, with respect to serious cardiopathy, at present, there may also be a case where the only way to cure such cardiopathy is with a heart transplant. Under such circumstances, a patient waiting for a heart transplant has to wait for a donor who is compatible with the patient. Accordingly, there may also be a case where the heart transplant cannot be promptly carried out thus causing a serious problem in maintaining the life of the patient waiting for a heart transplant.

Under such circumstances, recently, there has been proposed a method which assists the circulation of blood by embedding an artificial heart in a patient waiting for a heart transplant aiming at BTT (Bridge To Transplant). With the use of such an artificial heart, the patient waiting for a heart transplant can wait for a donor who is compatible with the patient for a long time. Further, at present, due to the enhancement of stability, reliability and the like of an artificial heart, attention has been focused on the use of an artificial heart aiming at BRT (Bridge To Recovery) which allows a patient to seek for the recovery of functions of his own heart. In fact, there have been many reports on cases in which a patient has recovered functions of his own heart by embedding of an artificial heart.

A technique has not been yet established which enhances the recovery of functions of a patient's own heart by the use of an artificial heart aiming at the use of BTR. However, there have been disclosed several artificial heart control techniques necessary for achieving the recovery of functions of the patient's own heart.

For example, patent document 1 discloses an artificial heart which regulates a load applied to a ventricle by providing an afterload regulatory chamber for temporarily storing blood ejected from the ventricle. Patent document 2 discloses, for example, an artificial heart which adjusts a rotational speed of a blood pump in response to a rapid change deviating from a normal operation range of a pump operation state in a continuous flow blood pump. Patent document 3 discloses an artificial heart which paces a ventricle in response to the presence or the non-presence of the occurrence of sticking of a blood removing cannula using a heart pacing function thus maintaining a cardiac rate of the patient's own heart above a certain specified number even at the time of wearing the artificial heart and thereby the sticking of the blood removing cannula, the occurrence of a thrombus and bradycardia or the like can be prevented. Further, for example, patent document 4 discloses a cardiac function evaluating device which evaluates a cardiac function by measuring a blood flow rate in a blood pump. Further, for example, patent document 5 discloses an artificial heart which lowers a rotational speed of a blood pump for suppressing the formation of a thrombus around the aortic valve. Further, non-patent document 1 discloses a technique on computer simulation in which the behavior of a continuous-flow-type blood pump when a rotational speed is changed is modeled.

PRIOR ART DOCUMENT

Patent Document

Patent document 1: brochure of International Publication 99/51285
Patent document 2: JP-A-2005-66013
Patent document 3: JP-A-2000-126282
Patent document 4: JP-A-2002-224066
Patent document 5: specification of US Patent Application 2005/0071001
Non-patent document 1
Non-patent document: Vandenverghe S. et al., "Unloading Effect of a Rotary Blood Pump Assessed by Mathematical Modeling", Artificial Organs, 27 (12), pp. 1094-1101, 2003

SUMMARY OF THE INVENTION

Problem to be Solved by the Invention

However, in the techniques disclosed in patent document 1 to patent document 5 and non-patent document 1, a rotational speed of a blood pump is changed on the basis of a fixed cardiac cycle irrespective of a length of a cardiac cycle of a patient's own heart and hence, an excessive or insufficient load for the patient's own heart is applied to the patient's own heart thus giving rise to a drawback that the recovery of functions of the patient's own heart may be impeded or blood cannot be sufficiently circulated.

The present invention has been made in view of such technical drawbacks, and it is an object to the present invention to provide an artificial heart control device, an artificial heart system and an artificial heart control method which can provide a load control optimum for the recovery of functions of the patient's own heart.

Means for Solving the Task

To overcome the above-mentioned drawbacks, the present invention provides an artificial heart control device for controlling a blood pump which assists flow of blood in a heart, the artificial heart control device including: a timing detection part which is configured to detect reference timing within a cardiac cycle of the heart; and a blood pump control part which is configured to control a rotational speed of the blood pump, wherein the blood pump control part controls, with reference to the reference timing detected by the timing detection part, the rotational speed of the blood pump such that the rotational speed becomes a rotational speed corresponding to a predetermined control pattern.

According to the present invention, the reference timing within the cardiac cycle of the heart is detected, and the rotational speed of the blood pump is controlled with reference to the reference timing such that the rotational speed becomes a rotational speed corresponding to the predetermined control pattern and hence, a load applied to a ventricle can be reduced in conformity with the cardiac cycle of the heart whereby the recovery of functions of the heart can be enhanced.

Further, in the artificial heart control device according to the present invention, the reference timing may be start timing of systole within the cardiac cycle.

According to the present invention, the reference timing can be detected easily and with high accuracy using a detection signal from a means which can be easily used such as a general-use electro cardiograph, for example, and hence, a load applied to a ventricle can be reduced easily and with high accuracy in conformity with a cardiac cycle of the heart whereby the recovery of functions of the heart can be further enhanced.

Further, in the artificial heart control device according to the present invention, the reference timing may be start timing of diastole within the cardiac cycle.

According to the present invention, the reference timing can be detected easily and with high accuracy using a detection signal from a means which can be easily used such as a blood-pressure gauge, for example, and hence, a load applied to a ventricle can be controlled easily and with high accuracy in conformity with a cardiac cycle of the heart whereby the recovery of functions of the heart can be further enhanced.

Further, in the artificial heart control device according to the present invention, the blood pump control part can control, with reference to the reference timing, the rotational speed of the blood pump such that a blood flow in the ventricle of the heart changes.

According to the present invention, blood staying within the ventricle of the heart can be suppressed so that the formation of the thrombus can be easily prevented.

Further, in the artificial heart control device according to the present invention, the blood pump control part can perform, with reference to the reference timing, a control in which the rotational speed of the blood pump is changed in accordance with a predetermined cyclic function within one or a plurality of cardiac cycles of the heart.

According to the present invention, a control is performed with reference to the reference timing such that the rotational speed of the blood pump is changed in accordance with the predetermined cyclic function within one or the plurality of cardiac cycles of the heart and hence, a load applied to the ventricle can be reduced in accordance with the degree of recovery of functions of the heart and in conformity with the cardiac cycle of the heart whereby the recovery of functions of the heart can be enhanced.

Further, in the artificial heart control device according to the present invention, the blood pump control part can control, with reference to the reference timing, the rotational speed of the blood pump such that the rotational speed of the blood pump is lowered in diastole of the heart, and the rotational speed of the blood pump is increased in systole of the heart.

According to the present invention, the artificial heart control device does not interrupt the movement of a cardiac muscle in diastole within a cardiac cycle while assisting the cardiac muscle in systole within the cardiac cycle and hence, the optimum assistance can be provided for respective cycles consisting of the systole and the diastole whereby the recovery of functions of the heart can be enhanced.

Further, in the artificial heart control device according to the present invention, the blood pump control part can control, with reference to the reference timing, the rotational speed of the blood pump such that an output flow rate of the blood pump becomes zero in systole of the heart, and a reverse flow rate of the blood pump becomes zero in diastole of the heart.

According to the present invention, even when the blood pump is a continuous-flow-type blood pump, a so-called OFF pump test which has not been easily realized so far can be easily realized and hence, a patient's risk can be reduced.

Further, in the artificial heart control device according to the present invention, the artificial heart control device includes an abnormality detection part which is configured to detect an abnormal state when the blood pump is being controlled, and the blood pump control part can control the rotational speed of the blood pump such that the rotational speed becomes a predetermined rotational speed when the abnormal state is detected by the abnormality detection part.

According to the present invention, the rotational speed of the blood pump is controlled, on a condition that the abnormal state is detected, such that the rotational speed becomes the predetermined rotational speed and hence, a load applied to a ventricle can be reduced in conformity with a cardiac cycle of a patient's heart whereby the recovery of the function of the patient's own heart can be enhanced, and the reliability of the artificial heart control device can be enhanced.

Further, in the artificial heart control device according to the present invention, the artificial heart control device includes a control pattern decision part which is configured to decide the control pattern based on a detection signal from a sensor which detects a state of a human body when the blood pump is being operated, and the blood pump control part can control, with reference to the reference timing detected by the timing detection part, the rotational speed of the blood pump such that the rotational speed becomes a rotational speed corresponding to the control pattern decided by the control pattern decision part.

According to the present invention, the control pattern is decided based on the detection signal from the sensor which detects a state of a human body when the blood pump is being operated, and a rotational speed of the blood pump is controlled with reference to the reference timing such that the rotational speed becomes the rotational speed corresponding to the control pattern and hence, a control of reducing a load applied to a ventricle in conformity with a cardiac cycle of a patient's heart can be dynamically performed whereby the recovery of functions of the heart can be further enhanced.

The present invention further provides an artificial heart system including: a blood pump which is configured to assist flow of blood in a heart; a sensor which is configured to detect a state of a human body when the blood pump is being operated; and the artificial heart control device described in any one of technical features described above for controlling the blood pump based on a detection signal from the sensor.

According to the present invention, it is possible to provide the artificial heart system which enables a load control optimum for the recovery of functions of the patient's own heart.

Further, in the artificial heart system according to the present invention, the blood pump includes a cannula distal end portion which is inserted into a left ventricle of the heart, and the blood pump can send out blood in the left ventricle to a main artery.

According to the present invention, it is possible to provide the artificial heart system having the blood pump which functions as a left ventricle assisting device which can perform a load control optimum for the recovery of functions of the patient's own heart.

The present invention still further provides an artificial heart control method for controlling a blood pump which assists flow of blood in a heart, the artificial heart control method including: a timing detection step in which reference timing within a cardiac cycle of the heart is detected; and a blood pump control step in which a rotational speed of the blood pump is controlled with reference to the reference timing detected in the timing detection step such that the rotational speed becomes a rotational speed corresponding to a predetermined control pattern.

Further, in the artificial heart control method according to the present invention, the reference timing may be start timing of systole within the cardiac cycle.

Further, in the artificial heart control method according to the present invention, the reference timing may be start timing of diastole within the cardiac cycle.

Further, in the artificial heart control method according to the present invention, in the blood pump control step, the rotational speed of the blood pump can be controlled with reference to the reference timing such that a blood flow in a ventricle of the heart changes.

Further, in the artificial heart control method according to the present invention, in the blood pump control step, a control in which the rotational speed of the blood pump is changed in accordance with a predetermined cyclic function within one or a plurality of cardiac cycles of the heart can be performed with reference to the reference timing.

Further, in the artificial heart control method according to the present invention, in the blood pump control step, the rotational speed of the blood pump can be controlled with reference to the reference timing such that the rotational speed of the blood pump is lowered in diastole of the heart, and the rotational speed of the blood pump is increased in systole of the heart.

Further, in the artificial heart control method according to the present invention, in the blood pump control step, the rotational speed of the blood pump can be controlled with reference to the reference timing such that an output flow rate of the blood pump becomes 0 in systole of the heart, and a reverse flow rate of the blood pump becomes 0 in diastole of the heart.

Further, in the artificial heart control method according to the present invention, the artificial heart control method includes an abnormality detection step in which an abnormal state when the blood pump is being controlled is detected and, in the blood pump control step, the rotational speed of the blood pump can be controlled such that the rotational speed becomes a predetermined rotational speed when the abnormal state is detected in the abnormality detection step.

Further, in the artificial heart control method according to the present invention, the artificial heart control method includes a control pattern decision step in which the control pattern is decided based on a detection signal from a sensor which detects a state of a human body when the blood pump is being operated and, in the blood pump control step, the rotational speed of the blood pump can be controlled with reference to the reference timing detected in the timing detection step such that the rotational speed becomes a rotational speed corresponding to the control pattern decided in the control pattern decision step.

According to any one of the above-mentioned inventions, it is possible to provide an artificial heart control method which can perform a load control optimum for the recovery of functions of a patient's own heart.

BEST MODE FOR CARRYING OUT THE INVENTION

Hereinafter, an embodiment of the present invention is explained in detail in conjunction with drawings. The embodiment explained hereinafter does not unduly limit contents of the present invention described in claims. Further, all constitutions explained hereinafter do not always constitute inevitable constitutional elements of the present invention.

Figure 1:
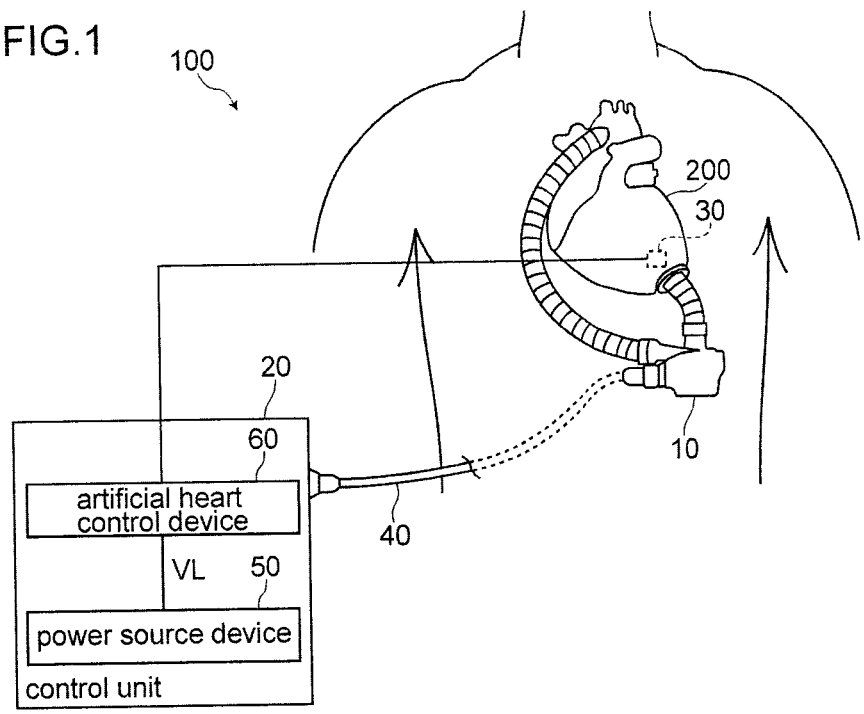
FIG. 1 is a view showing a constitutional example of an artificial heart system according to an embodiment of the present invention.

FIG. 1 shows a constitutional example of an artificial heart system according to an embodiment of the present invention.

The artificial heart system (a pump system, a motor system in broad meaning) 100 according to an embodiment of the present invention includes a blood pump (a pump, a motor, an artificial heart pump) 10, a control unit 20, and a sensor 30. The blood pump 10 and the control unit 20 are connected with each other by way of a cable 40. The sensor 30 is provided for detecting a state of a patient (human body) when the blood pump 10 is being operated. The sensor 30 is embedded in a patient's body, or is adhered to a patient's body surface or a surface of a patient's organ. A detection signal corresponding to a detection result of the sensor 30 is transmitted to the control unit 20 via a wired or wireless transmission medium.

The blood pump 10 functions as a left ventricular assist device (LVAD) which assists a function of a left ventricle of a patient's own heart 200. The blood pump 10 is a continuous-flow-type blood pump which produces the continuous flow of blood to be circulated.

The control unit 20 includes a power source device 50 and an artificial heart control device 60, and is arranged outside the body. The power source device 50 supplies a power source voltage to the artificial heart control device 60 from any one of an AC power source, a built-in battery and an emergency battery via a power source line VL. The artificial heart control device 60 generates a drive current (a drive signal in broad meaning) which drives the blood pump 10 in response to a detection signal from the sensor 30 in a state where a power source voltage is supplied from the power source device 50. To be more specific, the artificial heart control device 60 controls a rotational speed of the blood pump 10 using the drive current generated by the artificial heart control device 60 in response to the detection signal from the sensor 30. The cable 40 has a signal line through which a drive current to be supplied to the blood pump 10 from the control unit 20 is transmitted.

Figure 2:
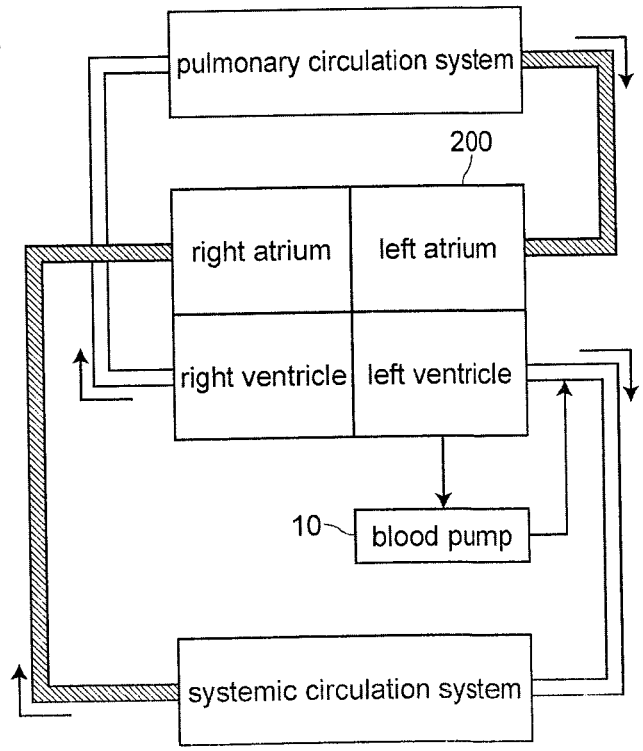
FIG. 2 is an explanatory view of a blood pump according to the embodiment.

FIG. 2 is an explanatory view of the blood pump 10 according to this embodiment. FIG. 2 schematically shows the patient's own heart 200 and a circulation system in the body.

The patient's own heart 200 is partitioned into a left atrium, a left ventricle, a right atrium and a right ventricle. The right atrium and the right ventricle have a function of circulating blood through a pulmonary circulation system, and the left atrium and the left ventricle have a function of circulating blood through a systemic circulation system. That is, the blood which is returned to the heart from the systemic circulation system through a superior vena cava and an inferior vena cava is stored in the right atrium and, thereafter, is sent to the right ventricle. The blood which is sent to the right ventricle circulates through the pulmonary circulation system through a pulmonary trunk by the beating of the right ventricle, and is brought into a state where the blood contains oxygen. The blood which is returned to the heart from the pulmonary circulation system through pulmonary veins is stored in the left atrium and, thereafter, is sent to the left ventricle. The blood which is sent to the left ventricle circulates through the systemic circulation system through a main artery by the beating of the left ventricle. The blood pump 10 according to this embodiment, for assisting the function of the left ventricle, sucks the blood which is sent to the left ventricle, and sends out the blood to the main artery.

Figure 3:
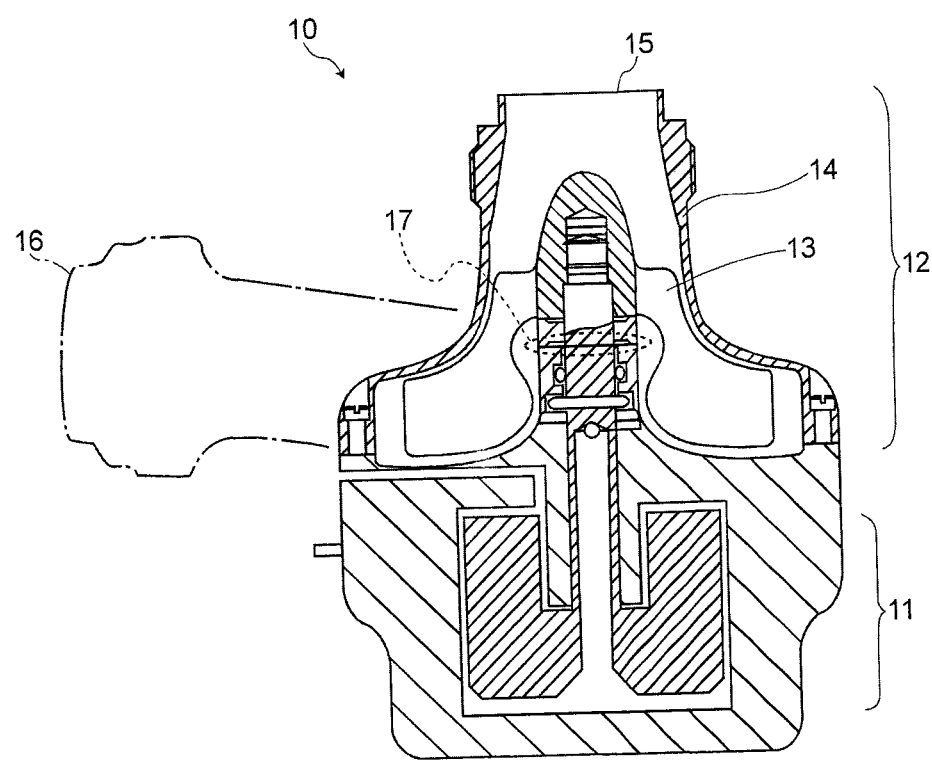
FIG. 3 is a view showing one example of a cross section of the blood pump according to the embodiment.

FIG. 3 shows one example of a cross section of the blood pump 10 according to this embodiment. Although FIG. 3 shows a constitutional example of a cross section of the blood pump 10, this embodiment is not limited to the blood pump having the constitution shown in FIG. 3.

The blood pump 10 includes a drive part 11 which has a cylindrical motor and a pump part 12 which is connected to the drive part 11. The pump part 12 includes an impeller 13 which is driven by way of a rotary shaft of the motor, and a pump casing 14 which is connected to the drive part 11 in a state where the pump casing 14 covers the impeller 13. The blood pump 10 is configured such that when blood in a left ventricle of a patient's own heart flows into the pump casing 14 via a blood vessel (artificial blood vessel) and an inflow port 15, after flow energy is imparted by the impeller 13, the blood flows out to a main artery via an outflow port 16 formed in a side surface of the pump casing 14 and a blood vessel (artificial blood vessel).

In the blood pump 10, a mechanical seal part 17 is arranged between the drive part 11 and the pump part 12. Accordingly, the pump part 12 and the drive part 11 are slidably and firmly sealed from each other thus suppressing leakage of the blood from the pump part 12 to the drive part 11 extremely well. As a result, the formation of a thrombus is suppressed thus suppressing stopping of an operation of the pump and a change in an operational state of the pump.

The pump part 12 is a centrifugal pump by which a larger blood flow rate can be expected than an axial flow pump, wherein a DC motor can be used as a motor for driving the impeller 13.

When the blood pump 10 is constituted as shown in FIG. 3, the control unit 20 shown in FIG. 1 further has a means for circulating a cool sealing liquid which suppresses the coagulation of blood in the mechanical seal part 17 and the generation of heat in the drive part 11 and the pump part 12. In this case, a circulation passage for the cool sealing liquid is formed by way of the cable 40.

The rotational speed of the blood pump 10 having the above-mentioned constitution is controlled corresponding to the cardiac cycle of the patient's own heart. Accordingly, the artificial heart control device 60 is configured to control the rotational speed of the blood pump 10 corresponding to the cardiac cycle of the patient's own heart based on a detection signal from the sensor 30.

Figure 4:
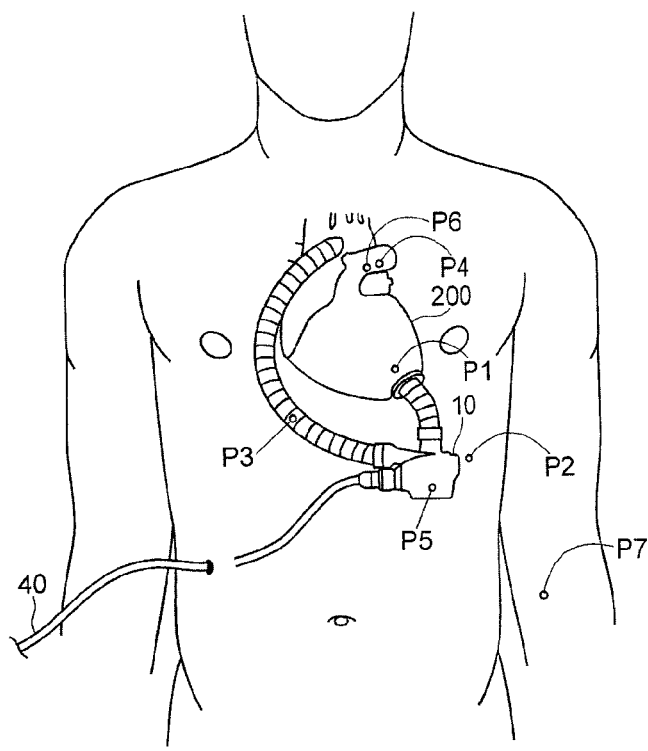
FIG. 4 is an explanatory view of a sensor according to the embodiment.

FIG. 4 is an explanatory view of the sensor 30 of this embodiment. In FIG. 4, parts identical with the parts shown in FIG. 1 are given same symbols and their explanation is omitted when appropriate. FIG. 4 schematically shows a mounting example of the sensor 30 on a patient's body, but the sensor 30 according to the present invention is not limited to the sensor shown in FIG. 4.

The sensor 30 according to this embodiment is mounted on a patient's body, the blood pump 10 or the like depending on an object to be detected.

The sensor 30 preferably detects at least one of, for example, an electrocardiogram, a blood flow rate and a blood pressure of the patient's own heart 200, an operation state of the blood pump 10, and other measured values having high correlation with a cardiac cycle.

For example, as shown in FIG. 4, an electrocardiograph lead line and a special cannula are mounted as the sensor 30 on a part for fixing a cannula to be inserted into a left ventricle of the patient's own heart 200 or at a position P1 on the periphery of the part, and an electrocardiograph amplifier is mounted in the artificial heart control device 60 of the control unit 20 so as to amplify a detection signal from the sensor 30 whereby the artificial heart control device 60 can acquire a detection signal corresponding to an electrocardiogram of the patient's own heart 200.

Alternatively, an electrocardiograph lead line and a special cannula are mounted on a body surface as the sensor 30 at a position P2 near the patient's own heart 200, for example, and an electrocardiograph amplifier is mounted in the artificial heart control device 60 of the control unit 20 so as to amplify a detection signal from the sensor 30 whereby the artificial heart control device 60 can acquire a detection signal corresponding to a body surface electrocardiogram of the patient's own heart 200.

The electrocardiogram or the body surface electrocardiogram of the patient's own heart 200 measured inside the patient's body or on the patient's body surface in this manner changes in response to the beats of the patient's own heart 200 and hence, it is possible to detect the cardiac cycle of the patient's own heart 200 based on the electrocardiogram or the body surface electrocardiogram.

Further, for example, as shown in FIG. 4, an ultrasonic or electromagnetic flowmeter may be mounted as the sensor 30 at a position P3 of a cannula which sends out blood taken out from the patient's own heart 200 to the main artery by the blood pump 10, and an flowmeter amplifier may be mounted in the artificial heart control device 60 of the control unit 20 so as to amplify a detection signal from the sensor 30 whereby the artificial heart control device 60 can acquire a detection signal corresponding to a discharge quantity of the blood pump 10.

Alternatively, for example, an ultrasonic or electromagnetic flowmeter may be mounted as the sensor 30 at a position P4 of a main artery of the patient's own heart 200, and an flowmeter amplifier may be mounted in the artificial heart control device 60 of the control unit 20 so as to amplify a detection signal from the sensor 30 whereby the artificial heart control device 60 can acquire a detection signal corresponding to a blood flow rate of main artery of the patient's own heart 200.

A discharge quantity of the blood pump 10 changes corresponding to systole and diastole within a cardiac cycle of the patient's own heart 200, and a blood flow rate of the main artery also changes corresponding to systole and diastole within a cardiac cycle of the patient's own heart 200. Accordingly, it is possible to detect the cardiac cycle of the patient's own heart 200 based on the blood flow rate of the blood pump 10 or the blood flow rate of the main artery. It may be possible to detect the blood flow rate of the pulmonary trunk and to detect the cardiac cycle of the patient's own heart 200 based on the detection signal.

Further, as shown in FIG. 4, for example, by mounting a rotational speed meter or an electric current sensor as the sensor 30 at a predetermined position P5 in the inside of the blood pump 10 or the control unit 20, the artificial heart control device 60 can acquire a detection signal corresponding to an actually measured rotational speed of the blood pump 10, a detection signal corresponding to power consumption of the blood pump 10 or a detection signal corresponding to an estimated flow rate of the blood pump 10.

The actually measured rotational speed of the blood pump 10, the power consumption of the blood pump 10 or the estimated flow rate of the blood pump 10 changes corresponding to systole and diastole within a cardiac cycle of the patient's own heart 200 and hence, it is possible to detect the cardiac cycle of the patient's own heart 200 based on the power consumption of the blood pump 10 or the estimated flow rate of the blood pump 10.

Further, for example, as shown in FIG. 4, a voltage transducer may be mounted as the sensor 30 at a position P6 of the main artery of the patient's own heart 200, and a voltage transducer amplifier may be mounted in the inside of the artificial heart control device 60 of the control unit 20 so as to amplify a detection signal from the sensor 30 and hence, the artificial heart control device 60 can acquire a detection signal corresponding to main-arterial blood pressure.

Alternatively, for example, a voltage transducer may be mounted as a sensor 30 at a position P7 of a body surface of a patient, and a voltage transducer amplifier may be mounted in the inside of the artificial heart control device 60 of the control unit 20 so as to amplify a detection signal from the sensor 30 and hence, the artificial heart control device 60 can acquire a detection signal corresponding to arterial blood pressure.

The main-arterial blood pressure or the arterial blood pressure changes corresponding to systole or diastole within a cardiac cycle of the patient's own heart 200 and hence, it is possible to detect the cardiac cycle of the patient's own heart 200 based on the main-arterial blood pressure or the arterial blood pressure. It may also be possible to detect a ventricle pressure and to detect a cardiac cycle of the patient's own heart 200 based on a detection signal.

Further, for example, as shown in FIG. 4, a conductance catheter which measures a volume of the inside of a ventricle of the patient's own heart 200 may be mounted as the sensor 30, and a conductance catheter device may be mounted in the inside of the artificial heart control device 60 of the control unit 20 and hence, the artificial heart control device 60 can acquire a detection signal corresponding to the volume of the ventricle.

The volume of the ventricle changes corresponding to systole or diastole of a cardiac cycle of the patient's own heart 200 and hence, it is possible to detect the cardiac cycle of the patient's own heart 200 based on the volume of the ventricle. Beside the above-mentioned means, it may be possible to detect photoelectric pulse wave, for example, and to detect a cardiac cycle of the patient's own heart 200 based on the detection signal.

The detection signal from the sensor 30 mounted in the inside of the patient's body or on the patient's body surface described above is outputted to the artificial heart control device 60 of the control unit 20, and the artificial heart control device 60 detects reference timing for specifying a cardiac cycle.

Figure 5:
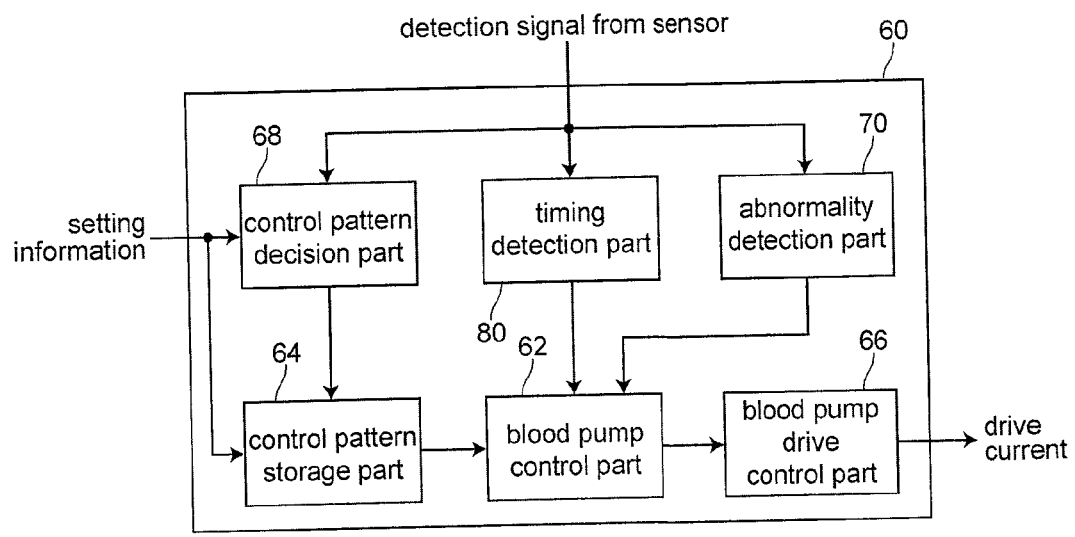
FIG. 5 is a block diagram of a constitutional example of an artificial heart control device according to the embodiment.

FIG. 5 is a block diagram of a constitutional example of the artificial heart control device 60 according to this embodiment.

Figure 6:
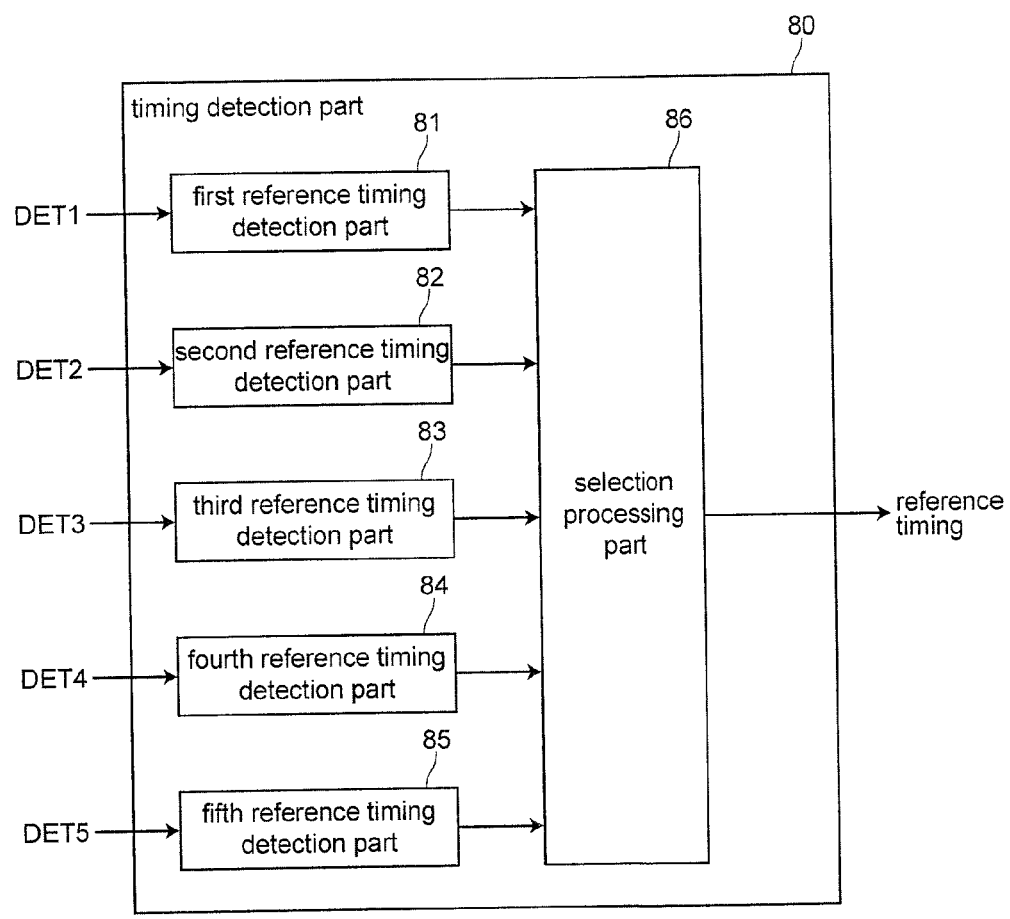
FIG. 6 is a block diagram of a constitutional example of a timing detection part shown in FIG. 5.

FIG. 6 is a block diagram of a constitutional example of a timing detection part 80 shown in FIG. 5. In FIG. 6, parts identical with the parts shown in FIG. 5 are given same symbols and their explanation is omitted when appropriate.

Figure 7:
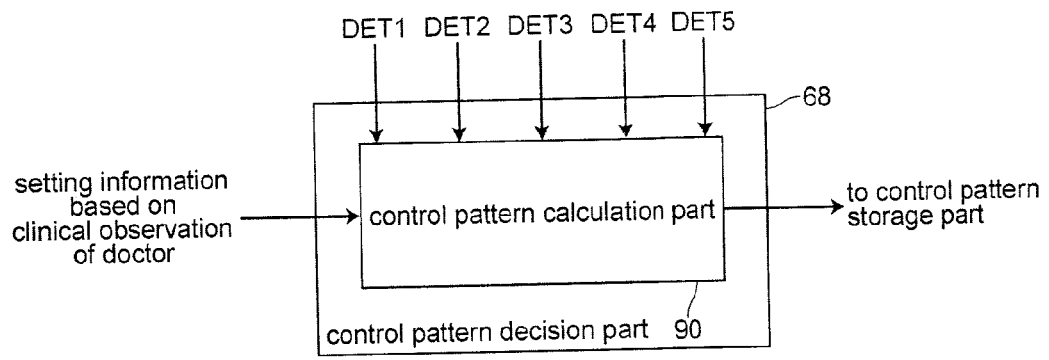
FIG. 7 is a block diagram of a constitutional example of a control pattern decision part shown in FIG. 5.

FIG. 7 is a block diagram of a constitutional example of a control pattern decision part 68 shown in FIG. 5. In FIG. 7, parts identical with the parts shown in FIG. 5 are given same symbols and their explanation is omitted when appropriate.

As shown in FIG. 5, the artificial heart control device 60 includes the timing detection part 80, a blood pump control part 62, a control pattern storage part 64, a blood pump drive control part 66, the control pattern decision part 68 and an abnormality detection part 70.

The timing detection part 80 acquires a detection signal from at least one sensor selected from sensors mounted at mounting positions shown in FIG. 4, and detects reference timing within a cardiac cycle of the patient's own heart 200 based on the detection signal. By deciding one reference timing within one cardiac cycle, it is possible to specify the cardiac cycle of the patient's own heart 200.

It is desirable that the reference timing within the cardiac cycle is suitably selected within the cardiac cycle in response to an object to be detected by the sensor 30. For example, when the sensor 30 can easily detect start timing of the cardiac cycle, it is desirable to adopt the start timing of the cardiac cycle as the reference timing. Further, a cardiac cycle includes so-called systole and diastole and hence, for example, when the sensor 30 can easily detect start timing of the systole within the cardiac cycle, it is desirable to adopt the start timing of the systole within the cardiac cycle as the reference timing. On the other hand, for example, when the sensor 30 can easily detect start timing of the diastole within the cardiac cycle, it is desirable to adopt the start timing of the diastole within the cardiac cycle as the reference timing.

In this embodiment, as shown in FIG. 6, the timing detection part 80 includes first to fifth reference timing detection parts 81 to 85 and a selection processing part 86. The timing detection part 80 selects one reference timing within a cardiac cycle out of reference timings detected by plural kinds of detection methods, and identifies a cardiac cycle using the reference timing.

A first detection signal DET1 (for example, electrocardiograph measurement signal) is inputted to the first reference timing detection part 81, and the first reference timing detection part 81 detects reference timing within a cardiac cycle of the patient's own heart 200 based on the first detection signal DET1. A second detection signal DET2 (for example, blood flow rate measurement signal) is inputted to the second reference timing detection part 82, and the second reference timing detection part 82 detects reference timing within a cardiac cycle of the patient's own heart 200 based on the second detection signal DET2. A third detection signal DET3 (for example, power consumption measurement signal of the blood pressure pump) is inputted to the third reference timing detection part 83, and the third reference timing detection part 83 detects reference timing within a cardiac cycle of the patient's own heart 200 based on the third detection signal DET3. A fourth detection signal DET4 (for example, blood pressure measurement signal) is inputted to the fourth reference timing detection part 84, and the fourth reference timing detection part 84 detects reference timing within a cardiac cycle of the patient's own heart 200 based on the fourth detection signal DET4. A fifth detection signal DET5 (for example, ventricle volume measurement signal) is inputted to the fifth reference timing detection part 85, and the fifth reference timing detection part 85 detects reference timing within a cardiac cycle of the patient's own heart 200 based on the fifth detection signal DET5. As such a detection signal, a ventricle inner pressure measurement signal from a sensor which detects a ventricle inner pressure may also be used.

The selection processing part 86 selects, based on a selection control signal not shown in the drawing, one reference timing out of the reference timings detected by the first to fifth reference timing detection parts 81 to 85 respectively. As the selection control signal, it may be possible to instruct the selection of the reference timing which the reference timing detection part to which the highest priority is assigned in accordance with the order of priority among the first to fifth reference timing detection parts 81 to 85 detect, for example.

In FIG. 6, the explanation has been made with respect to the case where one reference timing is selected from the reference timings detected by five kinds of reference timing detection parts. However, it may be possible to select one reference timing from the reference timings detected by 2 to 4 kinds, or 6 kinds or more reference timing detection parts. Further, the timing detection parts 80 may include only one reference timing detection part, and the reference timing detected by the reference timing detection part may be adopted as an output of the timing detection part 80.

In FIG. 5, the blood pump control part 62 controls, with reference to the reference timing detected by the timing detection part 80, a rotational speed of the blood pump 10 such that the rotational speed becomes a rotational speed corresponding to a predetermined control pattern. To be more specific, the blood pump drive control part 66 generates a drive current corresponding to instruction content from the blood pump control part 62, and a rotational speed of the blood pump 10 is controlled using the drive current. The blood pump control part 62 may incorporate a function of such a blood pump drive control part 66 therein.

The control pattern which the blood pump control part 62 looks up is stored in the control pattern storage part 64. The control pattern may be a pattern in which control information which designates a rotational speed of the blood pump 10 for each of a plurality of periods which are defined by dividing a cardiac cycle is set, for example. Such a control pattern may be directly set in the control pattern storage part 64 as setting information based on a clinical observation of a doctor, or may be decided by the control pattern decision part 68.

As shown in FIG. 7, the control pattern decision part 68 includes a control pattern calculation part 90. The control pattern decision part 68 acquires a detection signal from at least one sensor out of the sensors mounted on the mounting positions shown in FIG. 4 or setting information based on a clinical observation of a doctor, decides a control pattern in accordance with a predetermined pattern decision function (pattern decision algorism) based on the detection signal or the setting information, and stores the control pattern in the control pattern storage part 64.

The control pattern calculation part 90 calculates, based on detection values (measurement values) specified by the first to fifth detection signals DET1 to DET5, a control pattern for controlling a rotational speed of the blood pump 10 within one or a plurality of cardiac cycles. For example, the control pattern calculation part 90 calculates a control pattern in which a maximum value and a minimum value of a rotational speed of the blood pump 10, a period, a phase shift up to control start timing of a rotational speed using reference timing as the reference, a waveform which designates a manner of changing a rotational speed, frequency at which a rotational speed of the blood pump 10 is changed by Y times (Y being a natural number equal to X or less than X) for X pulses (X being a natural number equal to 1 or more than 1) and the like are specified. The control pattern calculated in this manner is stored in the control pattern storage part 64.

In FIG. 7, the explanation has been made with respect to the case where the control pattern is calculated based on 5 kinds of detection signals. However, the control pattern may be calculated based on 2 to 4 kinds, or 6 kinds or more of detection signals. Further, the control pattern calculation part 90 may calculate the above-mentioned control pattern based on only 1 detection signal.

In FIG. 5, the abnormality detection part 70 detects a abnormal state when the blood pump 10 is being controlled. As such an abnormal state, for example, a state where a range of a value of a detection signal from the sensor 30 falls outside a range of a normal value or a state where the deviation of a value of a detection signal from the sensor 30 exceeds a threshold value may be named. When an abnormal state is detected by the abnormality detection part 70, the blood pump control part 62 controls a rotational speed of the blood pump 10 such that the rotational speed becomes an instructed rotational speed. Here, it is desirable that the instructed rotational speed is a predetermined rotational speed. In this manner, when an abnormal state is detected during a control of a rotational speed of the blood pump 10 within a cardiac cycle based on a detection signal from the sensor 30, the blood pump control part 62 can continue the control of the blood pump 10 at the predetermined rotational speed irrespective of the detected reference timing so that the blood pump 10 can maintain a function of assisting the flow of blood in the patient's own heart 200 thus preventing a patient from falling into a critical condition.

In this embodiment, the artificial heart control device 60 may be configured by omitting one or a plurality of blocks from the blocks shown in FIG. 5. For example, the artificial heart control device 60 may be configured by omitting the control pattern decision part 68 from the constitution shown in FIG. 5.

Next, the manner of operation of the artificial heart control device 60 having the above-mentioned constitution is explained. Functions of the artificial heart control device 60 according to this embodiment may be realized by hardware or by software. In the explanation made hereinafter, assume that the functions of the artificial heart control device 60 according to this embodiment are realized by software processing.

Figure 8:
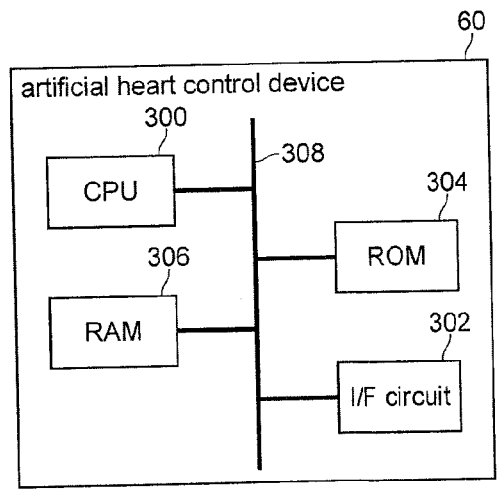
FIG. 8 is a block diagram of a hardware constitutional example of the artificial heart control device according to the embodiment.

FIG. 8 is a block diagram of a hardware constitutional example of the artificial heart control device 60 according to this embodiment.

The artificial heart control device 60 includes a CPU 300, an I/F circuit 302, a read only memory (ROM) 304, a random access memory (RAM) 306 and a bus 308. The CPU 300, the I/F circuit 302, the ROM 304 and the RAM 306 are electrically connected with each other via the bus 308.

For example, a program for realizing functions of the artificial heart control device 60 is stored in the ROM 304 or the RAM 306. The CPU 300 reads the program stored in the ROM 304 and the RAM 306, and executes processing corresponding to the program so that the CPU 300 can realize functions of the respective parts which constitute the artificial heart control device 60 by software processing. That is, the following processing is realized by the CPU 300 which reads the program stored in the ROM 304 or the RAM 306 and executes processing corresponding to the program. The RAM 306 is used as a working area of the processing by the CPU 300 or is used as a buffer area for the I/F circuit 302 and the ROM 304. The I/F circuit 302, as shown in FIG. 4, performs input/output interface processing between the artificial heart control device 60 and one or a plurality of sensors mounted in the inside of the patient's body or on the patient's body surface.

Figure 9:
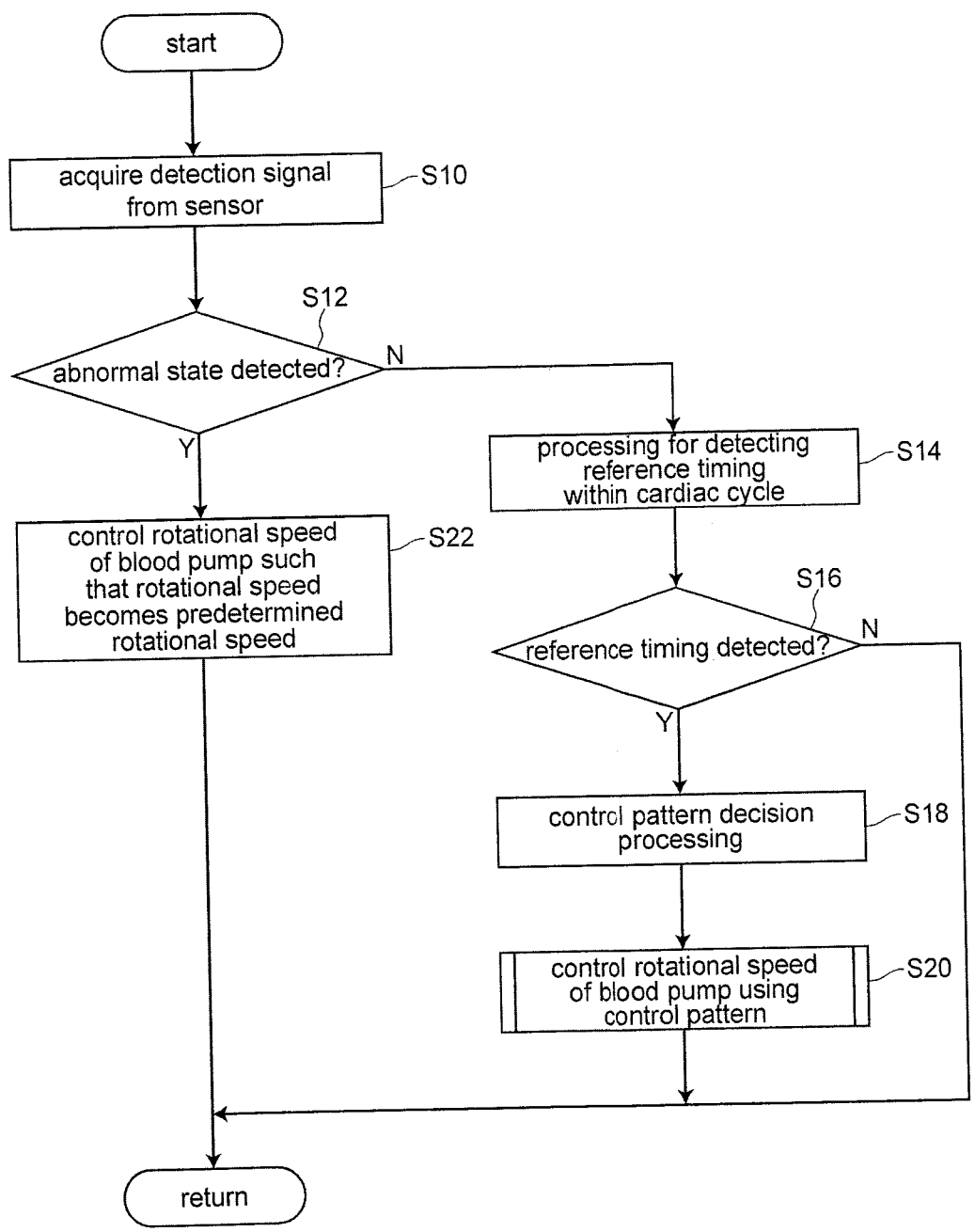
FIG. 9 is a flowchart of an example of processing performed by the artificial heart control device shown in FIG. 8.

FIG. 9 is a flowchart of an example of processing performed by the artificial heart control device 60 shown in FIG. 8.

Figure 10:
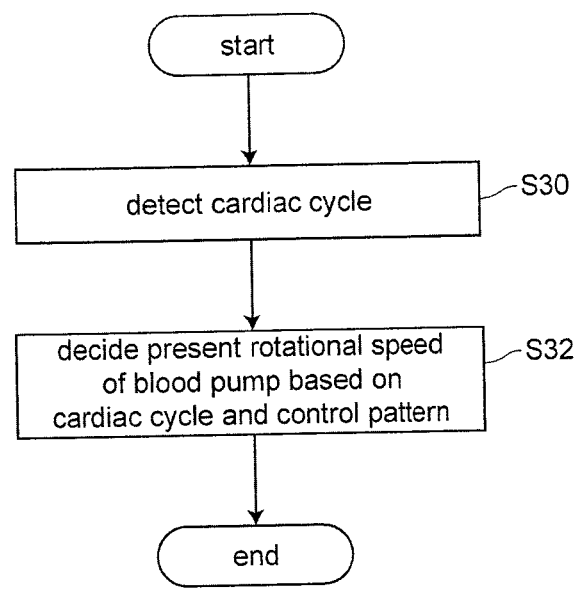
FIG. 10 is a flowchart of a detailed example of processing in step S20 shown in FIG. 9.

FIG. 10 is a flowchart of a detailed example of processing in step S20 shown in FIG. 9.

For example, a program for realizing the processing shown in FIG. 9 and FIG. 10 is stored in the ROM 304 or the RAM 306 shown in FIG. 8. When the CPU 300 reads the program stored in the ROM 304 or the RAM 306 and executes the processing corresponding to the program, the processing shown in FIG. 9 and FIG. 10 is realized by software processing.

Firstly, the artificial heart control device 60 acquires a detection signal from one or a plurality of sensors mounted in the inside of the patient's body or on the patient's body surface as shown in FIG. 4 (step S10). In an abnormality detection step, the artificial heart control device 60 executes abnormality detection processing in which the abnormality detection part 70 determines, for example, whether or not a value of a detection signal from the sensor falls within a normal value range which is set depending on a kind of the detection signal (step S12).

When an abnormal state is not detected in step S12 (step S12: N), in a timing detection step, the artificial heart control device 60 executes reference timing detection processing in which the timing detection part 80 detects reference timing within a cardiac cycle based on the detection signal acquired in step S10 (step S14).

When the reference timing within the cardiac cycle is detected in step S14 (step S16: Y), in a control pattern decision step, the control pattern decision part 68 of the artificial heart control device 60 decides the control pattern based on the detection signal from the sensor which detects a state of a human body when the blood pump is being operated, and the control pattern is stored in the control pattern storage part 64 (step S18).

Then, in a blood pump control step, the blood pump control part 62 of the artificial heart control device 60 reads the control pattern stored in the control pattern storage part 64 and controls a rotational speed of the blood pump 10 in accordance with the control pattern (step S20), and the processing returns to step S10 (return).

In step S20, as shown in FIG. 10, the blood pump control part 62 of the artificial heart control device 60 detects a cardiac cycle of the patient's own heart 200 and specifies start timing of a cardiac cycle based on the reference timing within the cardiac cycle detected in step S14 (step S30). Then, the blood pump control part 62, based on the cardiac cycle detected in step S30 and the control pattern decided in step S18, decides a present rotational speed of the blood pump 10 such that the rotational speed becomes a target rotational speed (step S32), and performs a control in which the blood pump control part 62 generates a drive current for the blood pump 10 which makes the rotational speed of the blood pump 10 acquire the above-mentioned target rotational speed (end). That is, the blood pump control part 62 controls, with reference to the reference timing detected in the timing detection step, the rotational speed of the blood pump such that the rotational speed becomes a rotational speed corresponding to the control pattern decided in the control pattern decision step.

On the other hand, when the reference timing within the cardiac cycle is not detected in step S14 (step S16: N), the artificial heart control device 60 does not control a rotational speed of the blood pump 10, and the processing directly returns to S10 (return).

Further, when the abnormal state is detected in step S12 (step S12: Y), in a blood pump control step, the blood pump control part 62 of the artificial heart control device 60 controls the rotational speed of the blood pump such that the rotational speed becomes a predetermined rotational speed (step S22), and the processing returns to step S10 (return).

Although the explanation is made in conjunction with FIG. 9 assuming that the control pattern is decided on a condition that the reference timing is detected, the present invention is not limited to the above-described case. For example, after the detection signal from the sensor is acquired in step S10, in the control pattern decision step, the control pattern decision part 68 of the artificial heart control device 60 may decide a control pattern based on the detection signal from the sensor which detects a state of a human body when the blood pump is being operated, and the control pattern may be stored in the control pattern storage part 64.

Further, although the explanation is made in conjunction with FIG. 9 and FIG. 10 assuming that the control pattern is decided in accordance with the detection signals from the sensors, the present invention is not limited to the above. For example, one or plural kinds of control patterns may be prepared in advance corresponding to the clinical observation of a doctor or values of various kinds of detection signals, and one control pattern may be selected based on the clinical observation of the doctor or the values of various kinds of detection signals.

Figure 11:
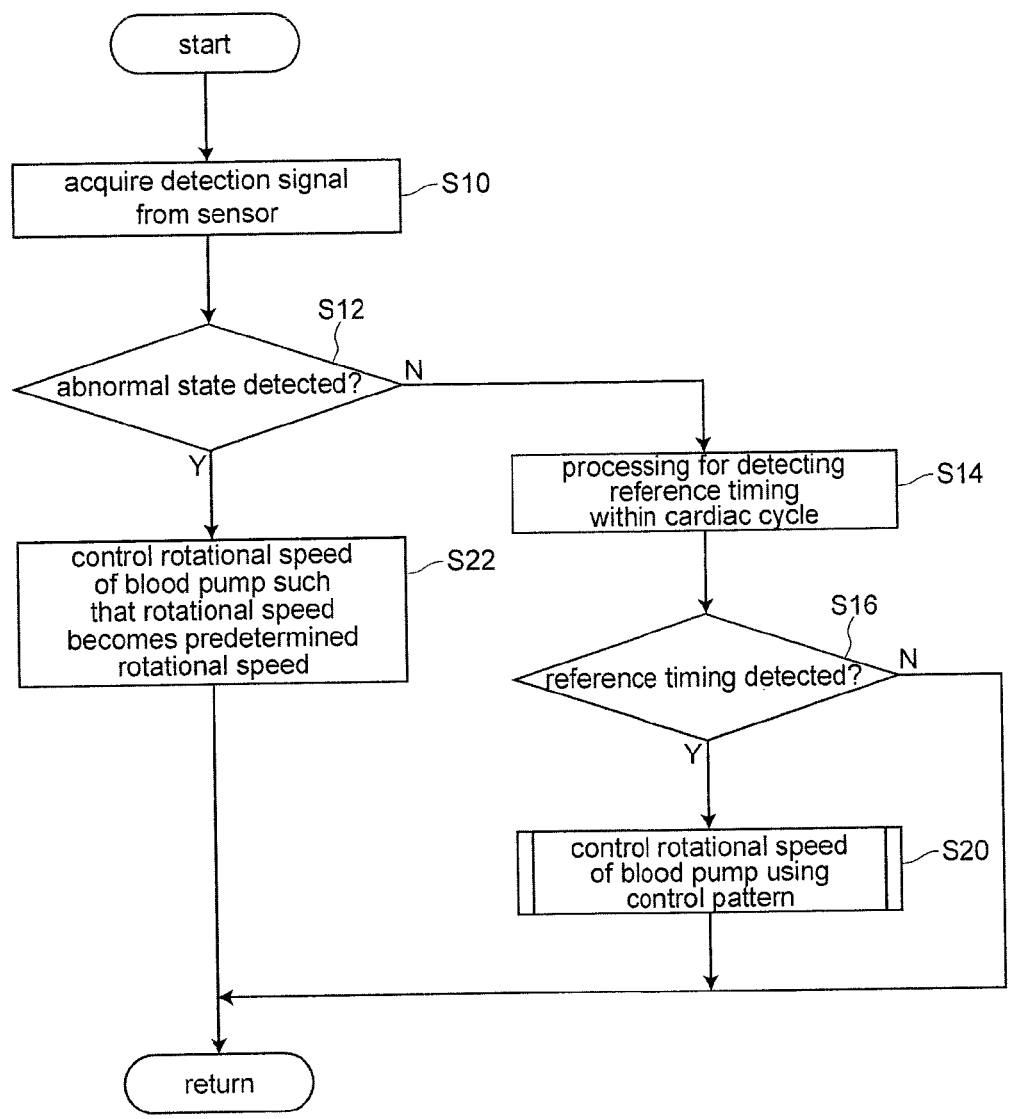
FIG. 11 is a flowchart of another example of processing performed by the artificial heart control device shown in FIG. 8 according to the embodiment.

FIG. 11 is a flowchart of another example of processing according to this embodiment performed by the artificial heart control device 60 shown in FIG. 8. In FIG. 11, steps which are identical with the steps in FIG. 9 are given same symbols, and their repeated explanation is omitted when appropriate.

In this case, for example, in the ROM 304 or the RAM 306 in FIG. 8, a program for realizing the processing shown in FIG. 10 and FIG. 11 is stored. When the CPU 300 reads the program stored in the ROM 304 or the RAM 306 and executes the processing corresponding to the program, the processing shown in FIG. 10 and FIG. 11 is realized by software processing.

A point which makes the processing flow shown in FIG. 11 differ from the processing flow shown in FIG. 9 lies in that step S18 is omitted. That is, when the reference timing within the cardiac cycle is detected in step S14 (step S16: Y), in a blood pump control step, the blood pump control part 62 of the artificial heart control device 60 reads a control pattern which is stored in the control pattern storage part 64 in advance in accordance with a detection signal and controls a rotational speed of the blood pump 10 in response to the control pattern (step S20), and the processing returns to step S10 (return).

Although it is a rare case, there have been reported cases where a patient whose blood flow in his own heart is assisted by an artificial heart system including this kind of artificial heart control device sufficiently recovers functions of his own heart. Accordingly, it has become also important to enhance the recovery of functions of a patient's own heart using an artificial heart system.

However, in this kind of artificial heart control device, the blood pump is always operated at a predetermined rotational speed or a rotational speed of the blood pump is changed irrespective of a cardiac cycle. Accordingly, in systole or diastole within the cardiac cycle, a load imposed on a ventricle is excessively or insufficiently reduced whereby the artificial heart control device obstructs the recovery of functions of the patient's own heart to the contrary.

In view of such circumstances, according to this embodiment, as described above, the reference timing within the cardiac cycle is detected, and the control of the blood pump 10 corresponding the control pattern is performed based on the reference timing whereby a load imposed on the ventricle is reduced in conformity with the cardiac cycle of the patient's own heart thus enhancing the recovery of functions of the patient's own heart.

Hereinafter, a specific operation example of the artificial heart control device 60 according to the present invention is explained. For the sake of facilitating the explanation, assume that the sensor 30 is constituted of just one electrocardiograph, and the timing detection part 80 detects the reference timing based on only a detection signal from the electrocardiograph.

Figure 12:
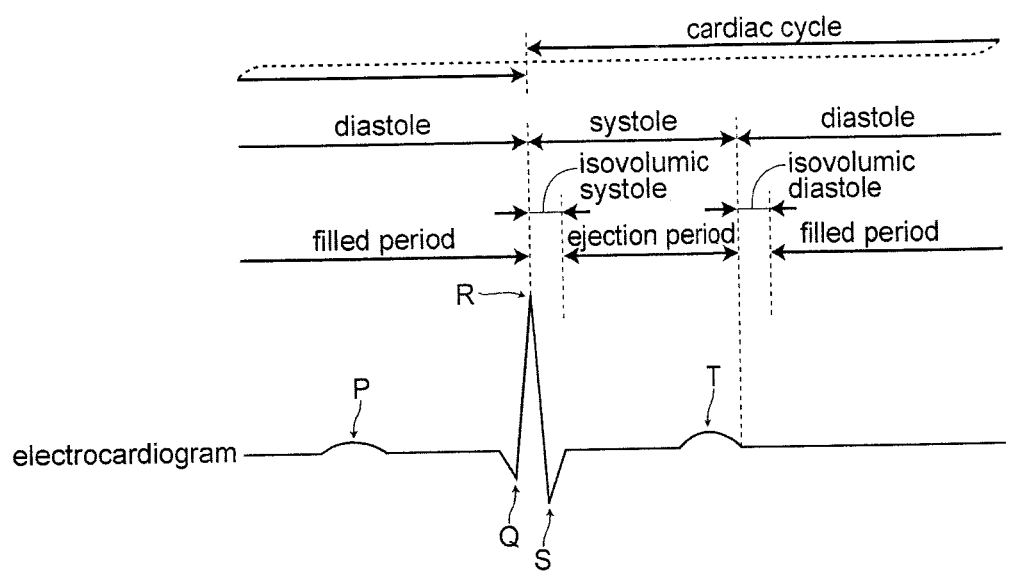
FIG. 12 is a timing chart schematically showing a general relationship between an electrocardiogram and a cardiac cycle according to the embodiment.

FIG. 12 schematically shows the general relationship between the electrocardiogram and the cardiac cycle according to this embodiment.

One beat of the patient's own heart 200 can be identified by measuring the manner in which an electric signal which is generated at a sinoatrial node is transmitted. For example, an electric signal which is generated at the sinoatrial node is transmitted to an atrium muscle so as to contract an atrium whereby a P wave shown in FIG. 12 is generated. Accordingly, the atrium is contracted so that an internal pressure of the atrium is elevated and a QRS wave is generated in conformity with a contraction period of the ventricle. Thereafter, a T wave is generated when the ventricle expands.

Here, a period from R to the completion of the T wave is referred to as systole within a cardiac cycle, and a period from the completion of the systole to R of the next beat is referred to as diastole within the cardiac cycle. The systole includes isovolumic systole in which tension is applied to a cardiac muscle in a state where an arterial valve and a valve between an atrium and a ventricle are closed, and an ejection period which comes after the isovolumic systole and is a period in which the arterial valve is opened in a state where the valve between the atrium and the ventricle is closed so that blood is sent out from the ventricle. Further, the diastole includes isovolumic diastole in which the ventricle is relaxed in a state where the arterial valve and a valve between an atrium and a ventricle are closed, and a filling period which is a period in which the valve between the atrium and the ventricle is open in a state where the arterial valve is closed so that blood is stored in the ventricle.

As can be clearly understood from FIG. 12, when an electrocardiograph is adopted as the sensor 30, it is possible to easily detect R in FIG. 12. Accordingly, in this case, the start timing of the systole (isovolumic systole) within the cardiac cycle can be easily detected as the reference timing, and the detection of the start timing can be carried out with high accuracy.

The reference timing in this embodiment is not limited to the start timing of the systole. For example, the start timing of the diastole within the cardiac cycle may be detected as the reference timing. In this case, by detecting the reference timing based on a blood pressure of main-arterial blood pressure or arterial blood pressure, the start timing of the diastole can be easily detected, and the detection of the start timing can be carried out with high accuracy. In this manner, with respect to the timing to be detected as the reference timing within a cardiac cycle, it is desirable to suitably select such timing corresponding to a kind of sensor 30.

FIG. 13(a) to FIG. 13(e) show examples of the control pattern according to this embodiment. FIG. 13(a) to FIG. 13(e) show the control patterns in which an axis of abscissas indicates a time axis, and an axis of ordinates indicates a waveform of an electrocardiogram and a rotational speed of the blood pump 10. The control patterns for carrying out controls shown in FIG. 13(a) to FIG. 13(e) may be directly stored in the control pattern storage part 64 or decided by the control pattern decision part 68 as setting information based on a clinical observation of a doctor.

In this embodiment, the blood pump control part 62 of the artificial heart control device 60, as shown in FIG. 13(a) to FIG. 13(e), performs, with reference to the reference timing within a cardiac cycle of a patient's own heart, a control in which a rotational speed of the blood pump 10 is changed in accordance with a predetermined periodic function within one or a plurality of cardiac cycles of a heart. Accordingly, it is desirable that a control pattern for controlling the blood pump control part 62 instructs a change of rotational speed of the blood pump 10 as follows.

Figure 13A:
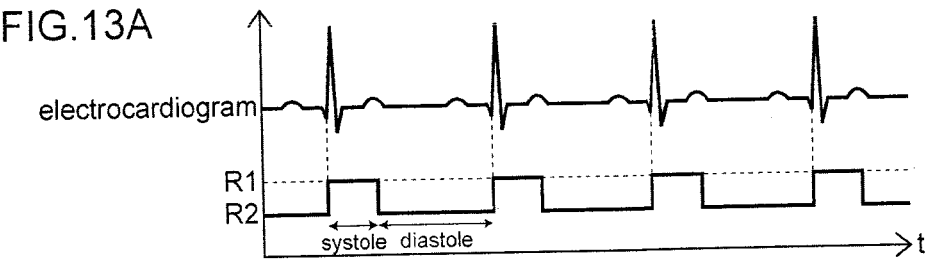
FIG. 13(a) to FIG. 13(e) are timing charts showing examples of a control pattern according to the embodiment.

FIG. 13(a) shows an example of the control pattern where a rotational speed of the blood pump 10 is changed during respective periods, that is, systole and diastole within a cardiac cycle. To be more specific, FIG. 13(a) shows the example of the control pattern which makes an instruction where when the cardiac cycle is specified based on a detection signal from an electrocardiograph, the rotational speed of the blood pump 10 becomes R1 (R1 being a positive number) in systole within the cardiac cycle, and the rotational speed of the blood pump 10 becomes R2 (R1>R2>0, R2 being a positive number) in diastole within the cardiac cycle. That is, FIG. 13(a) shows the control pattern which instructs the control of decreasing the rotational speed of the blood pump in diastole within the cardiac cycle.

In this manner, by controlling the rotational speed of the blood pump 10 with reference to the reference timing such that the rotational speed of the blood pump 10 is lowered in diastole of the heart and the rotational speed of the blood pump 10 is increased in systole of the heart, it is possible to allow the artificial heart control device to assist the cardiac muscle in systole and to prevent the artificial heart control device from impeding the movement of the cardiac muscle in diastole whereby the artificial heart control device can enhance the recovery of functions of the patient's own heart without applying an excessive load to the patient's own heart.

Figure 13B:
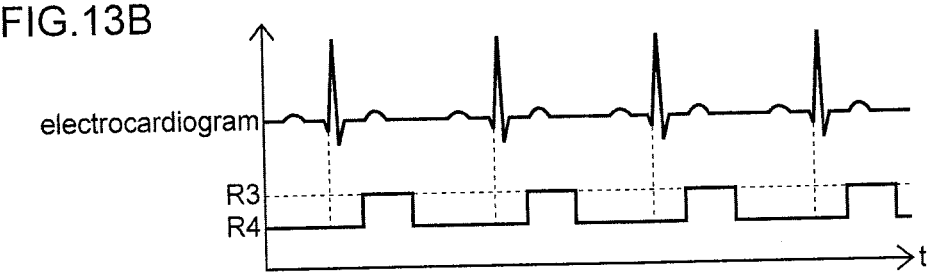

FIG. 13(b) shows an example of the control pattern where a rotational speed of the blood pump 10 is changed during respective periods, that is, systole and diastole within a cardiac cycle and, at the same time, the change timing of the rotational speed is shifted. To be more specific, FIG. 13(b) shows the example of the control pattern which makes an instruction where when the cardiac cycle is identified based on a detection signal from an electrocardiograph, the rotational speed of the blood pump 10 becomes R3 (R3 being a positive number) with a delay of a predetermined period from start timing of systole within the cardiac cycle, the rotational speed of the blood pump 10 becomes R4 (R3>R4>0, R4 being a positive number) with a delay of a predetermined period from start timing of diastole within the cardiac cycle.

In this manner, by changing a load in conformity with the cardiac cycle of the patient's own heart and by shifting the change timing, it is possible to make the proper load control in conformity with current functions of the patient's own heart and the enhancement of the recovery of functions of the patient's own heart compatible with each other.

Figure 13C:
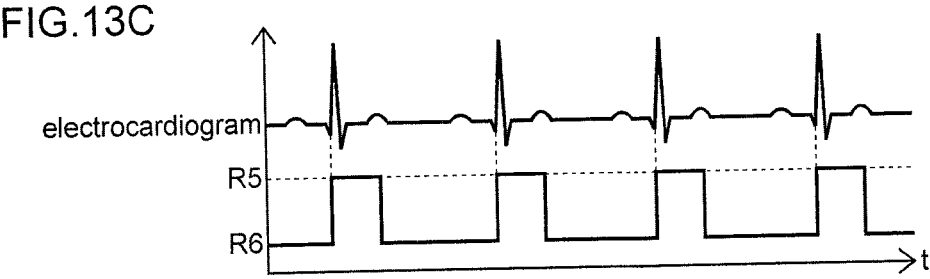

FIG. 13(c) shows an example of the control pattern where a rotational speed of the blood pump 10 is changed during respective periods, that is, systole and diastole within a cardiac cycle so that a rotational-speed change region is increased compared to a rotational-speed change region shown in FIG. 13(a). To be more specific, FIG. 13(c) shows the example of the control pattern which makes an instruction where when the cardiac cycle is specified based on a detection signal from an electrocardiograph, the rotational speed of the blood pump 10 becomes R5 (R5>R1, R5 being a positive number) in systole within the cardiac cycle, and the rotational speed of the blood pump 10 becomes R6 (R2>R6, R5>R6>0, R6 being a positive number) in diastole within the cardiac cycle.

In this manner, it is desirable to control a rotational speed of the blood pump 10 by changing a change range of the rotational speed of the blood pump 10 in conformity with current functions of the patient's own heart.

Figure 13D:
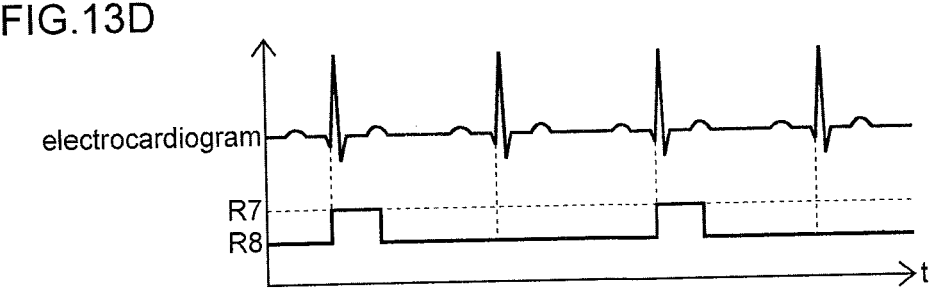

FIG. 13(d) is an example of the control pattern where a rotational speed of the blood pump 10 is changed by 1 (=Y) time for every 2 (=X) beats. To be more specific, FIG. 13(d) shows the example of the control pattern which makes an instruction where when the cardiac cycle is identified based on a detection signal from an electrocardiograph, the rotational speed of the blood pump 10 becomes R7 (R7, R7 being a positive number) in systole within a first cardiac cycle out of two cardiac cycles, and the rotational speed of the blood pump 10 becomes R8 (R7>R8>0, R8 being a positive number) in diastole within the cardiac cycle and systole and diastole within the succeeding cardiac cycle.

In this manner, in the control pattern according to this embodiment, the rotational speed of the blood pump 10 may not be controlled for every cardiac cycle, and a control period of the rotational speed of the blood pump 10 may be shortened depending on the degree of the recovery of functions of the patient's own heart 200.

Figure 13E:
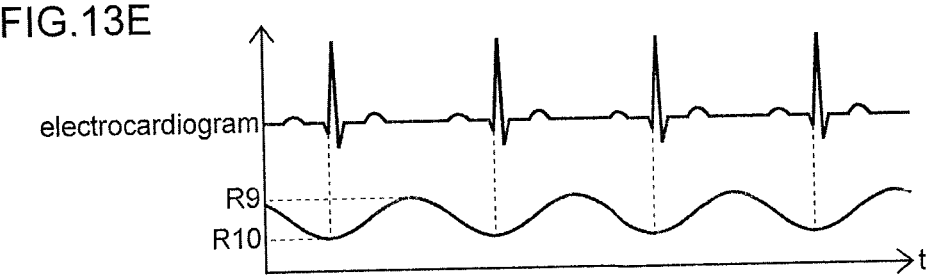

FIG. 13(e) shows an example of the control pattern where the rotational speed of the blood pump 10 is changed in a sinusoidal waveform. To be more specific, FIG. 13(e) shows the example of the control pattern which makes an instruction where when the cardiac cycle is identified based on a detection signal from an electrocardiograph, the rotational speed of the blood pump 10 is gradually increased in a sinusoidal waveform until the rotational speed becomes R9 (R9, R9 being a positive number) in systole within the cardiac cycle, and the rotational speed of the blood pump 10 is gradually lowered in a sinusoidal waveform until the rotational speed becomes R10 (R9>R10>0, R10 being a positive number) in diastole within the cardiac cycle. Although the rotational speed of the blood pump 10 is changed in a sinusoidal waveform in FIG. 13(e), the rotational speed is not limited to the waveform, and the rotational speed of the blood pump 10 may not be always changed in a square shape as can be understood from in FIG. 13(a) to FIG. 13(d).

As described above, according to this embodiment, the control in which the rotational speed of the blood pump 10 is changed in accordance with the predetermined periodic function within one or a plurality of cardiac cycles of the heart is performed with reference to the reference timing and hence, a load applied to a ventricle can be reduced in conformity with a cardiac cycle of a patient's own heart whereby the artificial heart control device can enhance the recovery of the functions of the patient's own heart.

Further, according to this embodiment, when there is a possibility that a rotational speed of the blood pump 10 becomes uncontrollable due to a malfunction of the sensor 30, abnormality of control algorithm or the like by any chance, the artificial heart control device has a mechanism which detects abnormality by an abnormality detection part 70, and forcibly changes an operation state of the artificial heart control device into a normal operation state where the blood pump 10 is operated at a predetermined rotational speed.

Figure 14A:
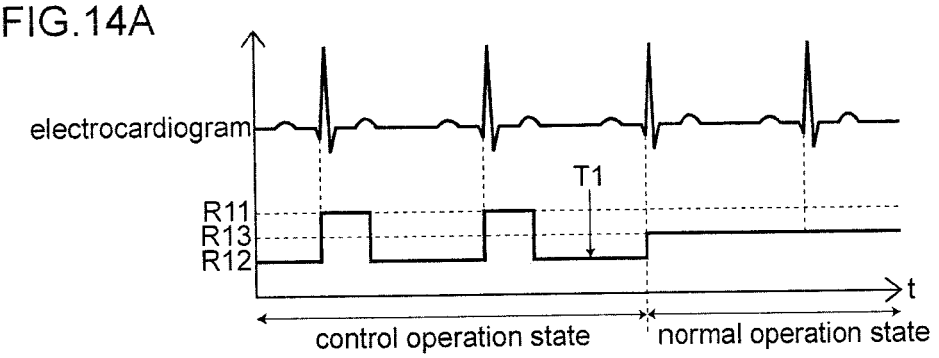
FIG. 14(a) and FIG. 14(b) are timing charts showing examples of processing which are executed at the time of detecting an abnormal state of the artificial heart control device according to the embodiment.
Figure 14B:
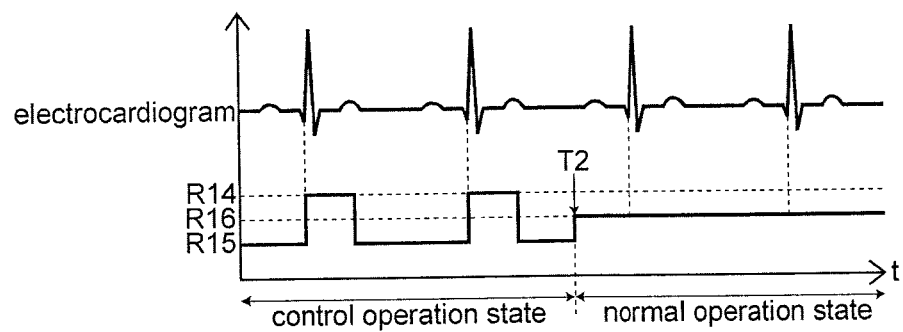

FIG. 14(a) and FIG. 14(b) show an example of processing when the artificial heart control device 60 according to this embodiment detects abnormality. FIG. 14(a) and FIG. 14(b) respectively show control patterns where an axis of abscissas indicates a time axis, and an axis of ordinates indicates a waveform of an electrocardiogram and a rotational speed of the blood pump 10.

In FIG. 14(a), when an abnormal state is detected at a point of time T1 in a control operation state in which the artificial heart control device 60 performs a control where, for example, start timing of systole within a cardiac cycle is detected as reference timing, a rotational speed of the blood pump 10 in the systole of the cardiac cycle is increased to R11 (R11 being a positive integer), and the rotational speed of the blood pump 10 in diastole of the cardiac cycle is lowered to R12 (R11>R12>0, R12 being a positive integer), the rotational speed of the blood pump 10 is controlled in a normal operation state from a point of time that next reference timing is detected. In this normal operation state, for example, a control is performed such that the rotational speed of the blood pump 10 is set to a predetermined value of R13 (R11>R13>R12). R13 may be set larger than R11 and smaller than R12.

Further, in FIG. 14(b), when an abnormal state is detected at a point of time T2 in a control operation state in which the artificial heart control device 60 performs a control where, for example, start timing of systole within a cardiac cycle is detected as reference timing, a rotational speed of the blood pump 10 in the systole of the cardiac cycle is increased to R14 (R14 being a positive integer), and the rotational speed of the blood pump 10 in diastole of the cardiac cycle is lowered to R15 (R14>R15>0, R15 being a positive integer), the rotational speed of the blood pump 10 is controlled in a normal operation state from a point of time that the abnormal state is detected. In this normal operation state, for example, a control is performed such that the rotational speed of the blood pump 10 is set to a predetermined value of R16 (R14>R16>R15). R16 may be set larger than R14 and smaller than R15.

As described above, according to this embodiment, on a condition that an abnormal state is detected, the artificial heart control device forcibly changes an operation state of the blood pump 10 into a normal operation state where the rotational speed of the blood pump 10 is set to a predetermined rotational speed (for example, the rotational speed being fixed) and hence, the reliability of the artificial heart system can be enhanced, and also a load imposed on a ventricle can be reduced in conformity with a cardiac cycle of a patient's own heart thus enhancing the recovery of functions of the patient's own heart.

Further, according to this embodiment having the above-mentioned constitution, by adopting the method which designates a rotational speed corresponding to a control pattern, the blood pump control part 62 can control, with reference to the reference timing, the rotational speed of the blood pump 10 such that the blood flow in the ventricle of the heart changes. Due to such a control, the artificial heart control device can acquire following advantageous effects.

Figure 15:
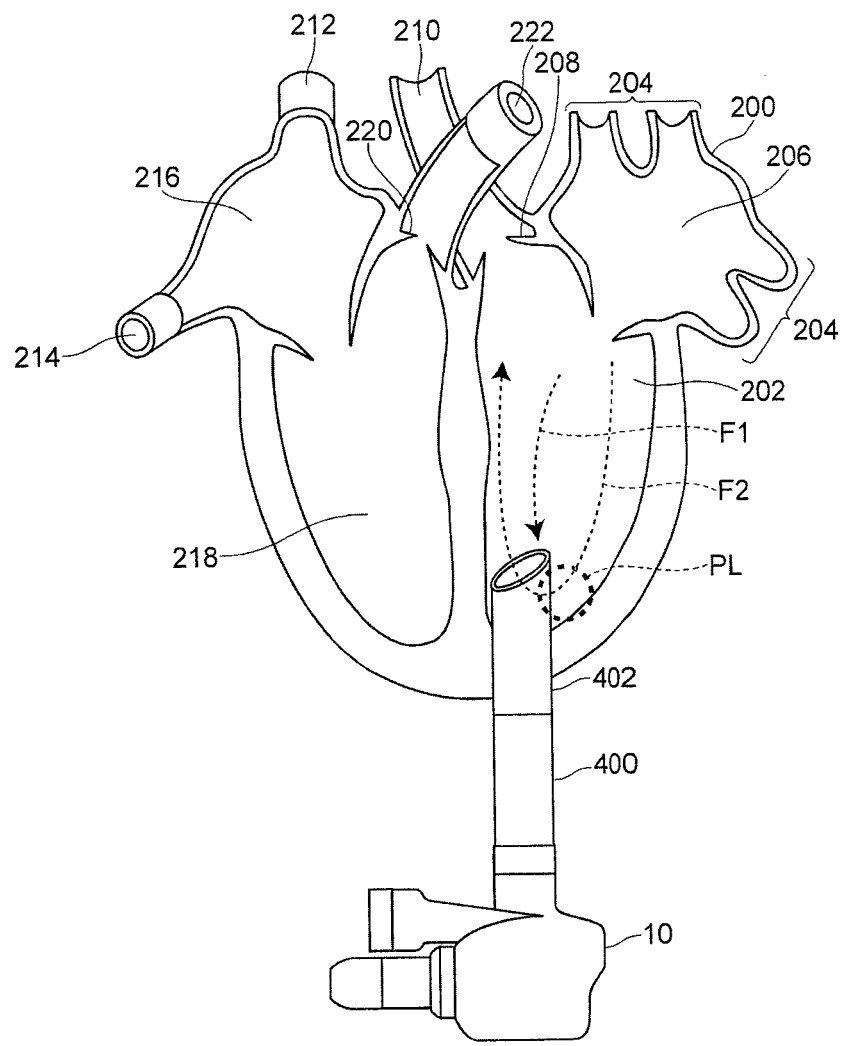
FIG. 15 is a view schematically showing a patient's own heart and the blood pump according to the embodiment.

FIG. 15 schematically shows the patient's own heart 200 and the blood pump 10 according to this embodiment. In FIG. 15, parts identical with the parts shown in FIG. 1 are given same symbols, and their explanation is omitted when appropriate.

As shown in FIG. 15, a cannula distal end portion 402 of the blood pump 10 is inserted into the inside of a left ventricle 202 of the patient's own heart 200 by way of a cannula graft portion 400 which constitutes a vascular graft. Blood which is returned to a left atrium 206 by way of a pulmonary vein 204 is sent to a left ventricle 202 when a mitral valve is opened. Then, a main arterial valve 208 is opened so that blood is sent to a main artery 210. Blood which is returned through a superior vena cava 212 and an inferior vena cava 214 by way of a systemic circulation system from the main artery 210 is stored in a right atrium 216, and when a tricuspid valve is opened, blood is sent to a right ventricle 218. Then, a pulmonary trunk valve 220 is opened so that blood is sent to a pulmonary trunk 222.

Here, to focus on the flow of blood sent to the left ventricle 202 from the left atrium 206, when the rotational speed of the blood pump 10 is a high rotational speed, as can be understood from the flow F1 shown in FIG. 15, blood which flows directly into the cannula distal end portion 402 from the left atrium 206 becomes a dominant flow. On the other hand, when the rotational speed of the blood pump 10 is a low rotational speed, as can be understood from the flow F2 shown in FIG. 15, there is a tendency that the blood flows along a wall of the left ventricle 202. Accordingly, blood is liable to stay in an area PL in the vicinity of a portion where the cannula distal end portion 402 is inserted and hence, a possibility that blood is solidified to form a thrombus is increased.

Accordingly, as described above, by allowing the blood pump control part 62 to control, with reference to the reference timing, a rotational speed of the blood pump 10 such that the blood flow in the ventricle of the heart is changed, it is possible to suppress the stay of blood in the area PL in the vicinity of the portion where the cannula distal end portion 402 is inserted thus preventing the formation of the thrombus.

Further, in an artificial heart system used in general, to check the degree of recovery of a patient's own heart, it is necessary to perform an OFF pump test in which a blood pump is stopped in a proper manner. However, although the OFF pump test can be easily realized by simply opening or closing valves in case of a beat-type blood pump, it is considered difficult to realize the OFF pump test in case of a continuous-flow (stationary-flow) blood pump.

However, according to this embodiment having the above-mentioned constitution, by adopting the method which designates a rotational speed corresponding to a control pattern, the blood pump control part 62 can control, with reference to the reference timing, the rotational speed of the blood pump 10 such that an output flow rate of the blood pump 10 becomes 0 in systole of a heart and a reverse flow rate of the blood pump 10 becomes 0 in diastole of the heart.

For example, by adopting a supersonic or electromagnetic flow meter or a rotational speed meter of a blood pump as the sensor 30 for detecting an output flow rate and a reverse flow rate of the blood pump 10, the control pattern decision part 68 may, based on the detection result, just decide a control pattern in which the rotational speed of the blood pump 10 is controlled with reference to the reference timing such that an output flow rate of the blood pump 10 becomes 0 in systole of a heart, and a reverse flow rate of the blood pump 10 becomes 0 in diastole of the heart. Then, the blood pump control part 62 controls the rotational speed of the blood pump 10 based on the control pattern. Due to such a control, even when the blood pump 10 used in an artificial heart system is a continuous flow type blood pump, an OFF pump test which has not been easily realized so far can be easily realized thus reducing a patient's risk.

Although the artificial heart control device, the artificial heart system and the artificial heart control method according to the present invention have been explained in conjunction with the above-mentioned embodiments heretofore, the present invention is not limited to the above-mentioned embodiments, and the invention can be carried out in various modes without departing from the gist of the present invention, and the following modifications are also conceivable, for example.

(1) In the above-mentioned embodiment, the explanation has been made assuming that the blood pump is a continuous flow type blood pump, however, the present invention is not limited to such a blood pump, and the blood pump may be a beat type blood pump which imparts a predetermined cycle to the flow of blood to be circulated. In this case, it becomes unnecessary to realize an OFF pump test using a control pattern.

(2) The blood pump according to the above-mentioned embodiment may be realized by an AC motor which is driven using a three-phase drive signal, a motor which is driven by a drive signal other than a three-phase drive signal, for example, or a DC motor.

(3) The artificial heart system 100 of the above-mentioned embodiment may include a monitoring device when appropriate. It is desirable that the monitoring device displays information which a doctor and a patient himself can check such as a power source voltage of the control unit 20, operation states of the blood pump 10 (a drive current, a target rotational speed, an actual operation rotational speed and the like of the blood pump 10), a value of a detection signal from the sensor 30 and a cardiac cycle of the patient's own heart 200.

In the above-mentioned embodiment, the present invention has been explained with respect to the artificial heart control device, the artificial heart system and the artificial heart control method. However, the present invention is not limited to these objects. For example, the present invention is also applicable to a program in which processing steps of the artificial heart control method according to the present invention is described or a storage medium in which the program is stored.

EXPLANATION OF SYMBOLS

10: blood pump, 11: drive part, 12: pump part, 13: impeller, 14: pump casing, 15: inflow port, 16: outflow port, 17: mechanical seal part, 20: control unit, 30: sensor, 40: cable, 50: power source device, 60: artificial heart control device, 62: blood pump control part, 64: control pattern storage part, 66: blood pump drive control part, 68: control pattern decision part, 70: abnormality detection part, 80: timing detection part, 81: first reference timing detection part, 82: second reference timing detection part, 83: third reference timing detection part, 84: fourth reference timing detection part, 85: fifth reference timing detection part, 86: selection processing part, 90: control pattern calculation part, 100: artificial heart system, 200: patient's own heart, 202: left ventricle, 204: pulmonary vein, 206: left atrium, 208: main arterial valve, 210: main artery, 212: superior vena cava, 214: inferior vena cava, 216: right atrium, 218: right ventricle, 220: pulmonary trunk valve, 222: pulmonary trunk, 300: CPU, 302: I/F circuit, 304: ROM, 306: RAM, 308: bus, 400: cannula graft portion, 402: cannula distal end portion, DET1 to DET5: first to fifth detection signals, F1, F2: flow of blood, PL: area in the vicinity of portion where cannula distal end portion is inserted

The invention claimed is:

1. An artificial heart control device for controlling a blood pump which assists flow of blood in a heart, the artificial heart control device comprising:
- a timing detection part which is configured to detect reference timing within a cardiac cycle of the heart, based on a detection signal from a sensor to detect a state of a human body when the blood pump is being operated; and
- a blood pump control part which is configured to control a rotational speed of the blood pump, wherein
- the blood pump control part controls, with reference to the reference timing detected by the timing detection part, the rotational speed of the blood pump such that the rotational speed becomes a rotational speed corresponding to a predetermined control pattern,
- the artificial heart control device further comprises an abnormality detection part which is configured to detect an abnormal state of at least one of a patient, the blood pump, the sensor or the artificial heart control device when the blood pump is being controlled, and
- the blood pump control part controls the rotational speed of the blood pump such that the rotational speed becomes a predetermined rotational speed, which is set separately from the rotational speed corresponding to the predetermined control pattern under a normal state of the respective at least one of the patient, the blood pump, the sensor or the artificial heart control device, when the abnormal state is detected by the abnormality detection part.

2. The artificial heart control device according to claim 1, wherein the reference timing is start timing of systole within the cardiac cycle.

3. The artificial heart control device according to claim 1, wherein the reference timing is start timing of diastole within the cardiac cycle.

4. The artificial heart control device according to claim 1, wherein the blood pump control part controls, with reference to the reference timing, the rotational speed of the blood pump such that a blood flow in a ventricle of the heart changes.

5. The artificial heart control device according to claim 1, wherein the blood pump control part performs, with reference to the reference timing, a control in which the rotational speed of the blood pump is changed in accordance with a predetermined cyclic function within one or a plurality of cardiac cycles of the heart.

6. The artificial heart control device according to claim 1, wherein the blood pump control part controls, with reference to the reference timing, the rotational speed of the blood pump such that the rotational speed of the blood pump is lowered in diastole of the heart, and the rotational speed of the blood pump is increased in systole of the heart.

7. The artificial heart control device according to claim 1, wherein the blood pump control part controls, with reference to the reference timing, the rotational speed of the blood pump such that an output flow rate of the blood pump becomes 0 in systole of the heart, and a reverse flow rate of the blood pump becomes 0 in diastole of the heart.

8. The artificial heart control device according to claim 1, wherein
- the artificial heart control device further comprises a control pattern decision part which is configured to decide the control pattern based on a detection signal from a sensor which detects a state of a human body when the blood pump is being operated, and
- the blood pump control part controls, with reference to the reference timing detected by the timing detection part, the rotational speed of the blood pump such that the rotational speed becomes a rotational speed corresponding to the control pattern decided by the control pattern decision part.

9. The artificial heart control device according to claim 8, wherein
- the artificial heart control device further comprises a control pattern storage part in which the predetermined control pattern, which is decided by the control pattern decision part, is stored, and
- the blood pump control part controls the rotational speed of the blood pump based on the predetermined control pattern which is stored in the control pattern storage part.

10. An artificial heart system, comprising:
- a blood pump which is configured to assist flow of blood in a heart; and
- the artificial heart control device described in claim 1 for controlling the blood pump.

11. The artificial heart system according to claim 10, wherein
- the blood pump includes a cannula distal end portion which is inserted into a left ventricle of the heart, and
- the blood pump sends out blood in the left ventricle to a main artery.

12. The artificial heart system according to claim 10, further comprising:
- a sensor which is configured to detect a state of a human body when the blood pump is being operated, wherein
- the artificial heart control device is configured to control the blood pump based on a detection signal from the sensor.

13. The artificial heart system according to claim 12, wherein
- the blood pump includes a cannula distal end portion which is inserted into a left ventricle of the heart, and
- the blood pump sends out blood in the left ventricle to a main artery.

14. The artificial heart control device according to claim 1, wherein the blood pump control part is configured to continue the control of the blood pump at the predetermined rotational speed irrespective of the detected reference timing when the abnormal state is detected during a control of a rotational speed of the blood pump.

15. The artificial heart control device according to claim 1, wherein the timing detection part comprising:
- a plurality of reference timing detection parts in which each reference timing detection part is configured to detect each reference timing; and
- a selection processing part which is configured to select one reference timing, as the reference timing, out of the reference timings detected by the plurality of reference timing detection parts.

16. The artificial heart control device according to claim 1, wherein
- the artificial heart control device further comprises a control pattern storage part in which the predetermined control pattern is stored, and the blood pump control part controls the rotational speed of the blood pump based on the predetermined control pattern which is stored in the control pattern storage part.

17. The artificial heart control device according to claim 1, wherein the blood pump includes an impeller which is configured to impart a flow energy to the blood.

18. The artificial heart control device according to claim 1, wherein the reference timing is start timing of systole within the cardiac cycle, and the blood pump control part controls, with reference to the reference timing, the rotational speed of the blood pump such that an output flow rate of the blood pump becomes 0 in systole of the heart, and a reverse flow rate of the blood pump becomes 0 in diastole of the heart.

* * * * *